(12) United States Patent
Harder et al.

(10) Patent No.: US 12,102,741 B2
(45) Date of Patent: Oct. 1, 2024

(54) PROTECTIVE FACE MASK USING UVC LEDS

(71) Applicant: ATMOS Life Science, Inc., San Jose, CA (US)

(72) Inventors: Frank Bernd Juergen Harder, San Jose, CA (US); C. T. Chou, Oxfordshire (GB)

(73) Assignee: Atmos Life Sciences, Inc., San Jose, CA (US)

( * ) Notice: Subject to any disclaimer, the term of this patent is extended or adjusted under 35 U.S.C. 154(b) by 1043 days.

(21) Appl. No.: 17/004,989

(22) Filed: Aug. 27, 2020

(65) Prior Publication Data
US 2022/0016298 A1    Jan. 20, 2022

Related U.S. Application Data

(60) Provisional application No. 63/052,176, filed on Jul. 15, 2020.

(51) Int. Cl.
*A61L 9/20* (2006.01)

(52) U.S. Cl.
CPC ............ *A61L 9/20* (2013.01); *A61L 2209/111* (2013.01); *A61L 2209/14* (2013.01)

(58) Field of Classification Search
CPC ...... A41D 13/00; A41D 13/002; A41D 13/11; A61L 2/00; A61L 2/10; A61L 2209/11; A61L 2209/111; A61L 2209/10; A61L 2209/12; A61L 2209/14; A61L 2209/133; A61L 2209/212; A61L 9/20; A61B 7/00; A61B 7/10; A62B 9/00; A62B 18/00; A62B 18/02; A62B 18/025; A62B 18/04;

(Continued)

(56) References Cited

U.S. PATENT DOCUMENTS

| 10,335,618 B2 | 7/2019 | Zhou et al. |
| 2010/0132715 A1* | 6/2010 | Litz .......................... A62B 7/10 |
| | | 128/207.12 |

(Continued)

OTHER PUBLICATIONS

Totobobo Pte. Ltd. Singapore, "Singapore High Tech PM2.5 Air Pollution Respiratory Mask", accessed Aug. 25, 2020, 6 pages, <https://totobobo.com/>.

*Primary Examiner* — Ophelia A Hawthorne
*Assistant Examiner* — Gina McCarthy
(74) *Attorney, Agent, or Firm* — Patent Law Group; Brian Ogonowsky

(57) ABSTRACT

A protective mask for filtering out and effectively killing harmful organisms includes a transparent or translucent covering for the wearer's mouth. One or more resilient straps hold the covering over the wearer's mouth. Two modules, one at each edge of the covering, are located behind the edge of the eye sockets to reduce the moment of inertia when the wearer turns her head or moves her head up or down. Each module contains two UVC LEDs injecting light into a reflective chamber. A flow rate sensor in the chamber detects a flow rate of inhaled and exhaled air, and a controller supplies current to the LEDs generally proportional to the air flow. To remove heat from the LEDs, the LEDs are thermally coupled to heat sinks, a thermally conductive body of the modules, a thermally conductive grill, a thermally conductive receptacle for the modules, and thermally conductive straps.

15 Claims, 16 Drawing Sheets

(58) Field of Classification Search
CPC ......... A62B 18/08; A62B 23/00; A62B 23/02;
A42B 3/18; A42B 3/28; A42B 3/281;
A42B 3/285; A42B 3/286; A42B 3/288;
A61M 16/06; A61M 16/0683; F21L
4/027; A61N 5/0624
See application file for complete search history.

(56) References Cited

U.S. PATENT DOCUMENTS

| | | | | |
|---|---|---|---|---|
| 2013/0139816 | A1* | 6/2013 | Proctor | A62B 18/02 |
| | | | | 128/206.13 |
| 2013/0319417 | A1* | 12/2013 | Weinman | A61M 16/0683 |
| | | | | 128/205.25 |
| 2014/0288351 | A1* | 9/2014 | Jones | A61N 5/0624 |
| | | | | 607/90 |
| 2015/0192286 | A1* | 7/2015 | Hansen | F21L 4/027 |
| | | | | 362/373 |
| 2016/0001108 | A1* | 1/2016 | Zhou | A62B 7/10 |
| | | | | 128/863 |
| 2016/0317687 | A1* | 11/2016 | Dayton | A61L 2/10 |
| 2021/0228761 | A1* | 7/2021 | Kaneko | A61L 2/10 |
| 2021/0275714 | A1* | 9/2021 | Almeida | A62B 18/025 |
| 2023/0330452 | A1* | 10/2023 | Magar | A62B 23/02 |

* cited by examiner

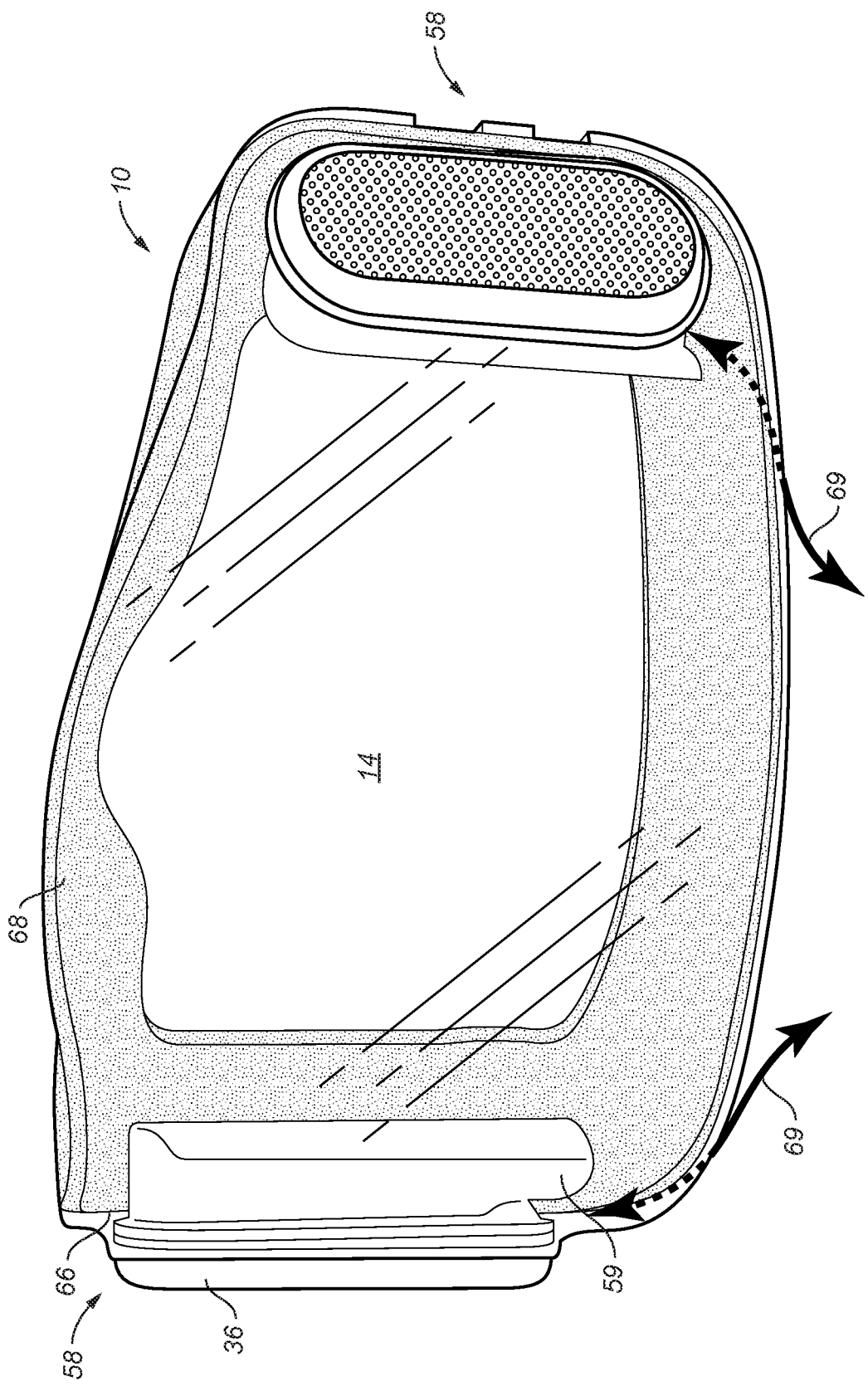

PROTECTIVE FACE MASK USING UVC LEDS

CROSS-REFERENCE TO RELATED APPLICATIONS

This application is based on and claims priority from U.S. provisional application Ser. No. 63/052,176, filed on Jul. 15, 2020, by Frank Harder et al.

FIELD OF THE INVENTION

The invention relates to reusable protective face masks for filtering air and for effectively killing pathogens, such as viruses and bacteria, using UVC LEDs.

BACKGROUND

Protective masks that provide mechanical air filtering and expose the air to UVC radiation are known. UVC radiation inactivates pathogens by modifying their genetic material, DNA and RNA. The current preferred wavelength for inactivation is about 265 nm, which is within the UVC range of 200-280 nm. The effectiveness and ways the UVC light effectively kill organisms are still being studied.

Mechanical filtration of air by a mask requires a tight seal around the face to prevent air being leaked out around the edges of the mask. Since viruses are very small (<0.1 micron), the effective pore size in the filter must be small, which restricts breathing.

If the mask is also equipped with a UVC light source, significant weight is added to the mask, such as by the UVC light source, a heat sink, battery, controller, special air passageways, etc. Such added weight is typically located in front of the wearer's face, which pulls down on the mask and creates a large moment of inertia when the wearer's head moves. This makes wearing the mask uncomfortable, which negatively impacts compliance rates.

What is needed is a combination of a mechanical air filtration mask and a UVC exposure mask that does not suffer from the drawbacks with prior art masks.

SUMMARY

A reusable protective mask for providing mechanical air filtration and UVC exposure to the incoming and outgoing air is disclosed. UVC LEDs are used along with electronics and other hardware needed for operation. An expected field of use is in health care and the food industry, where the cost of such a mask is justified.

The mask is relatively large in order to wrap around the face. Therefore, the compressive forces pulling the mask against the face are spread over a larger surface area and the mask is more securely positioned over the face. The mask may be translucent or transparent, so the wearer's face is minimally obscured. The translucency should be such that one can see the wearer's mouth movements when talking and the wearer's facial expression, which greatly improves understanding by the listener.

For reducing the mask's down-pulling moment, which causes the sensation of front-heaviness when worn, or reducing the moment of inertia when the wearer's head is moved, the LEDs and supporting elements are packaged in a small module on both sides of the mask, located as close as practical to the axes of rotation of the head. In other words, the modules are located at a "best fit" location close to the rotational axes of the head's up/down and sideways movements. This means that there is minimum angular momentum of the module when the wearer moves her head up, down, and sideways. In one embodiment, the modules are located along the back jaw line, well behind the nose and between the ear and the edge of the eye socket. It is adequate, however, that the modules are located approximately between the edge of the eye socket and the ear.

In another embodiment, there is only a single module if the UVC power is sufficient to adequately inactivate pathogens.

All air flows through the small module. A replaceable air filter is also optionally contained in the module.

The module includes an air flow rate sensor and a controller. The detection of air flow through the module results in the controller dynamically controlling current to the UVC LEDs to optimize battery life. For example, a higher current (e.g., a constant higher current or a higher average current) is supplied to the UVC LEDs during the detected peak inhalation and the peak exhalation times to most effectively inactivate organisms during both air flow directions based on the rate of air flowing through the module. The flow chamber has a reflective inner coating or separate liner to reflect the UVC light. The reflective liner may be a separate piece that is inserted into a metal outer housing.

For the most accurate flow reading, there should be a minimum of air turbulence in the reflective chamber. To accomplish this, the flow rate sensor is located near the point of entry of the inhaled air (where there is the least turbulence). Optionally, there may be a flow rate sensor on both sides of the UVC LEDs, so the flow rate is precisely detected in both flow directions. The LEDs are recessed in the chamber, or flush with the chamber walls, to present the minimum discontinuity in the chamber's smooth walls. In contrast, known prior art air disinfectant units promote turbulence to expose the maximum amount of air to the UVC light. However, the present inventive design creates low turbulence to provide a more accurate flow rate sensor reading. The UVC LEDs are relatively powerful (e.g., 100 mW optical power), so there is adequate exposure of the air to the UVC light in the small chamber.

Since the control current for the UVC LEDs is generally proportional to the flow of air, there may be periods of low air flow or rapid changes in air flow when the wearer is talking. To avoid the UVC LEDs blinking rapidly due to the rapid changes in air flow, which may cause early LED failures, a minimum steady current is supplied to the UVC LEDs when the air flow is below a certain threshold. This also preserves the battery life, since switching losses are reduced. The current supplied to the UVC LEDs may be controlled by varying the instantaneous (analog) current.

In another embodiment, the optical power output by the UVC LEDs is controlled by varying pulse-width modulation (PWM) (so that the most efficient instantaneous current level is supplied to the UVC LEDs).

A replaceable and rechargeable battery pack is located on the back strap of the mask to reduce the weight and size of the module. A flexible circuit tape or serpentine wires are encased in the strap for electrical connection to the module.

Heat is generated by the LEDs and electronics. To remove heat from the module, the LED chips are thermally mounted on a metal heat sink in the module. The module has a light weight, thermally conductive body, thermally coupled to the heat sink, that further spreads the heat. The materials used can be graphite, aluminum or copper alloys, thermally conductive ceramics such as aluminum nitride, or thinly laminated combinations thereof. The front of the module has an optional thermally conductive (e.g., etal) grill with a large surface area (due to a mesh or fin shape), so air flowing around the grill further conducts the heat to the air. Thermally conducting particles or strips are embedded in the resilient strap for the mask and the receptacle for the removable module that additionally conduct the heat. The particles or strips may be graphene, graphite, copper, aluminum, etc. A dense layer of thermally conductive particles may be laminated within layers of the silicone strap.

Other features of the mask are also described.

BRIEF DESCRIPTION OF THE DRAWINGS

FIG. 19 shows the modules of FIG. 15 installed in the mask, with a resilient seal between the modules and the mask, where all air between the mask and the ambient air flows through the bottom opening of module.

Elements labeled with the same numerals in the various figures may be identical or similar.

DETAILED DESCRIPTION

Figure 1:
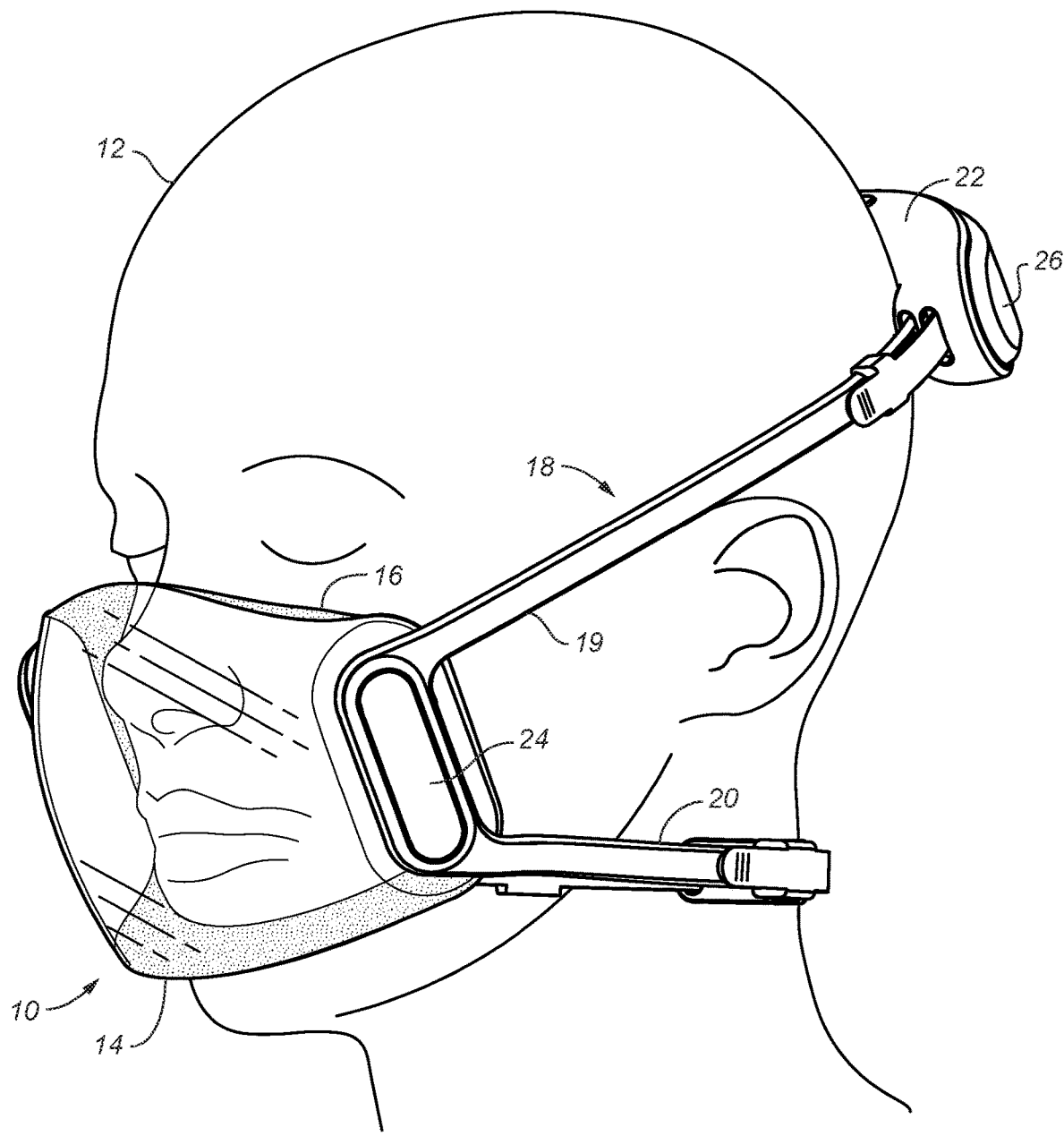
FIG. 1 is a side view of the mask in accordance with one embodiment of the invention. In other embodiments, the modules may be closer to the rear jaw line.
Figure 2:
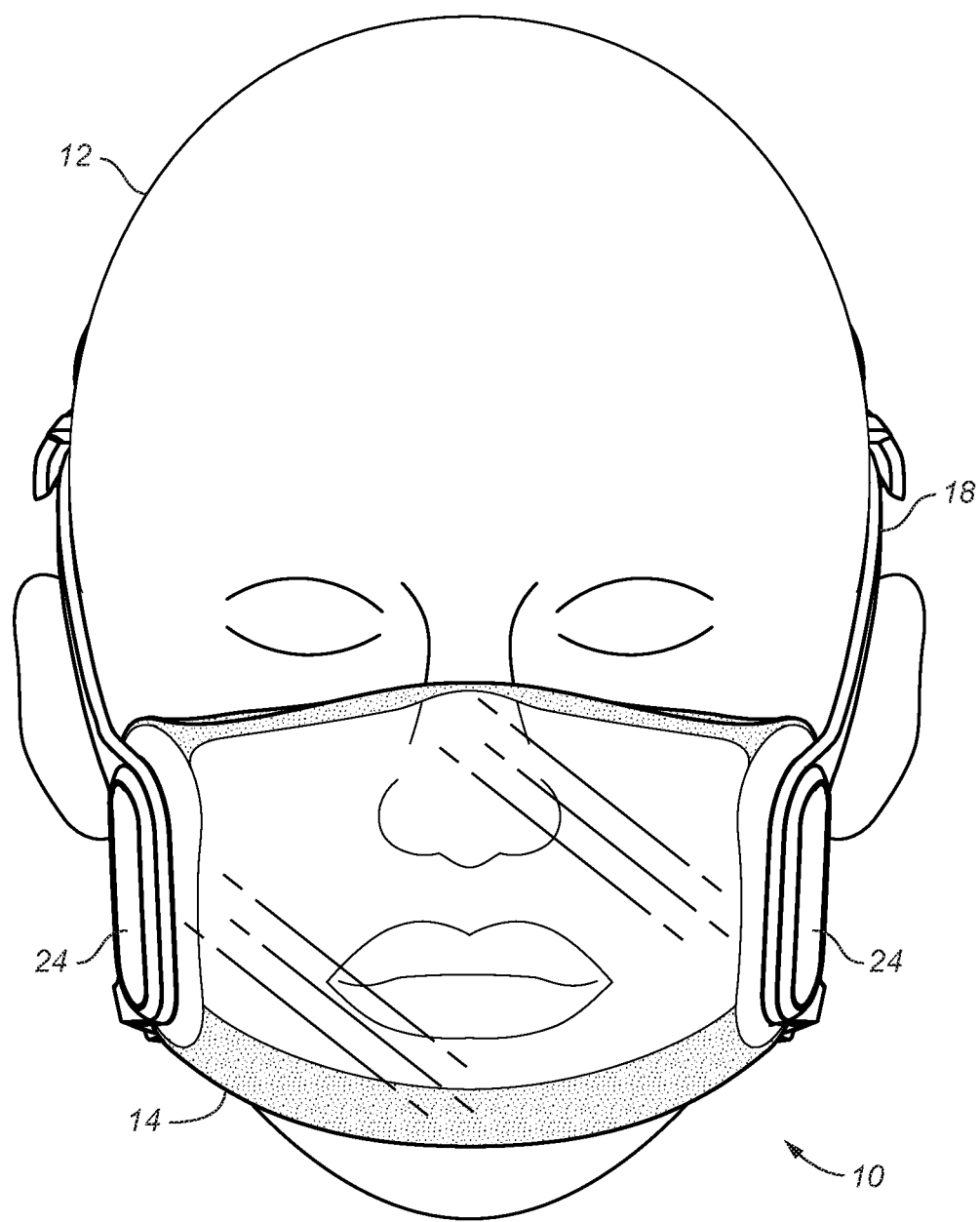
FIG. 2 is a front view of the mask.
Figure 3:
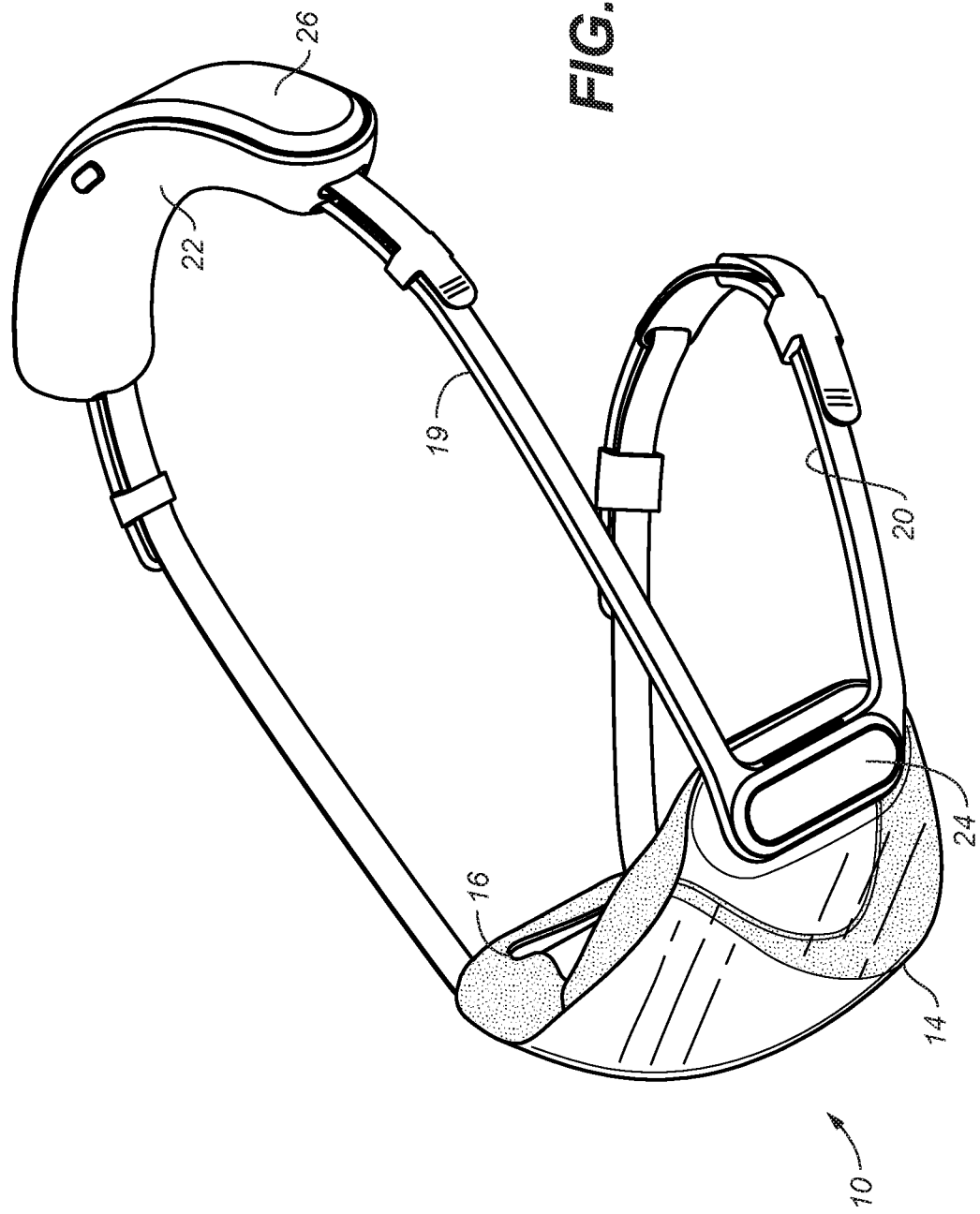
FIG. 3 shows the mask removed from the wearer.

FIG. 1 is a perspective view of a protective mask 10, in accordance with one embodiment of the invention, being worn by a user 12. FIG. 2 is a front view of the mask 10. FIG. 3 shows the mask 10 removed.

The mask 10 comprises a plastic, transparent or translucent nose/mouth cover 14. The translucency should be such that the wearer's mouth should be visible to aide in understanding what the wearer is saying and to sense the wearer's expression.

A soft silicone lip 16 is provided along the edges of the nose/mouth cover 14 to create a soft and air tight seal between the mask 10 and the wearer's face. The shape of the nose/mouth cover 14 may be customized to the wearer's face using facial-scan imaging technologies and 3D printing.

The mask 10 is supported in place by a resilient silicone strap 18, which comprises an upper strap 19 and a lower strap 20 for even pressure on the wearer's face with the forces shared by both straps 19 and 20. The straps 19/20 do not touch the user's ears. The strap lengths can be adjusted for achieving the proper pressure of the mask 10 on the wearer's face. A soft silicone pad 22 evenly distributes pressure and prevents the upper strap 19 from shifting.

The mask 10 is low enough to not interfere with the wearer's eyeglasses.

On both sides of the mask 10 are identical filtering and UVC exposure modules 24, discussed in detail later. The electronics in the modules 24 are powered by a removable battery 26 attached to the back of the silicone pad 22. Having separately driven identical modules provides an added layer of protection due to redundancy.

Optionally, a single-side module may be sufficient for low-cost considerations if the UVC optical power is sufficiently high.

Figure 4:
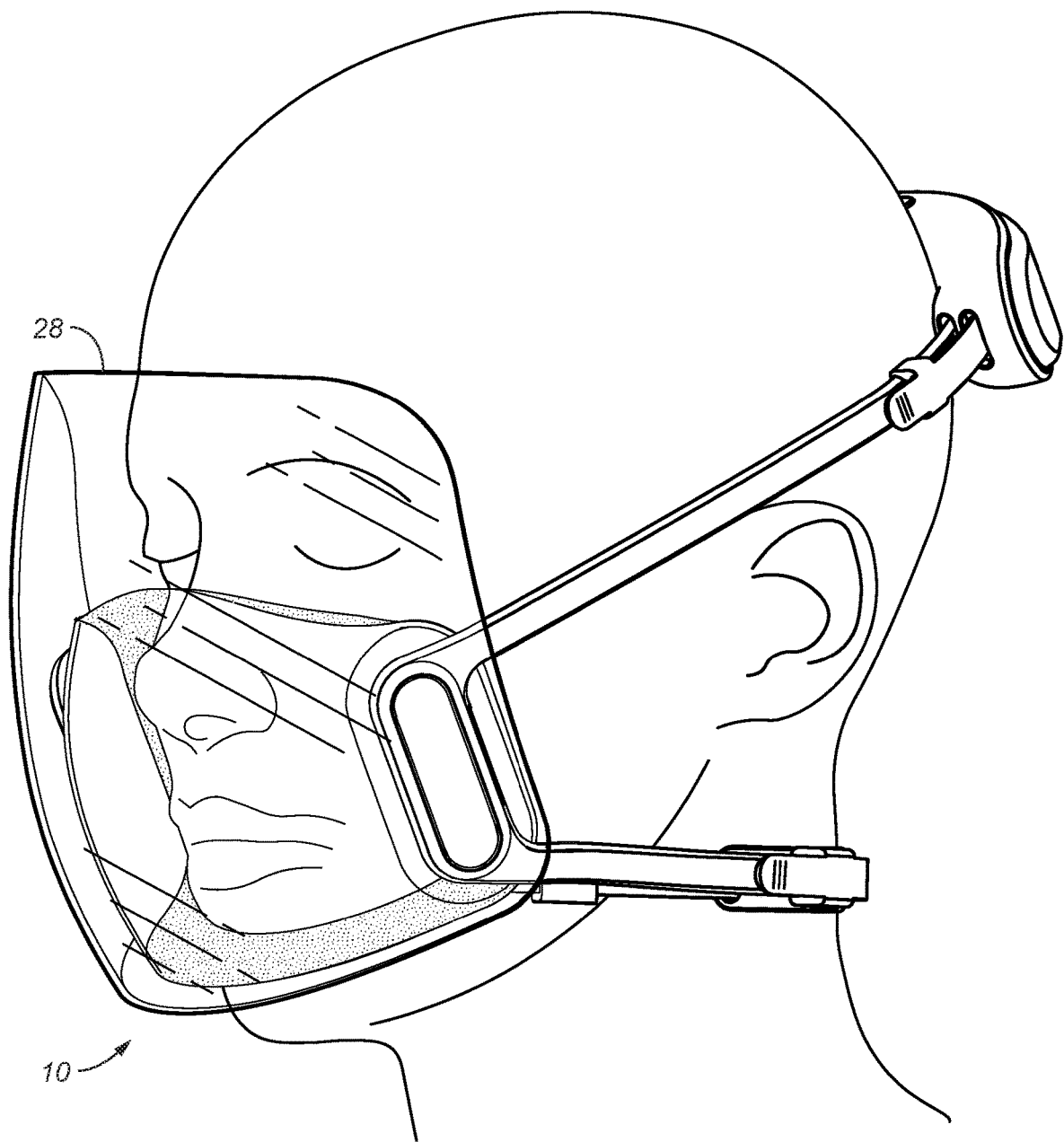
FIG. 4 illustrates the use of a removable face shield.

FIG. 4 illustrates the use of a protective shield 28 that is attachable to the mask 10 using magnets near the edges. The shield 28 protects the wearer's eyes.

The modules 24 includes UVC LEDs, heat sinks, an aluminum body, a reflective chamber for exposing the inhalation air and exhalation air to UVC light to inactivate at least 99.9% (e.g., 99.999%) of respiratory pathogens in the air, a flow rate sensor, power managements circuits, and filters. The UVC light is optionally multi-wavelength, depending on the particular vulnerabilities of one or more prevalent pathogens in an outbreak, such that inactivation against these particular species may be optimized. As such, the modules 24 have substantial mass that would be uncomfortable if located at the front of the mask 10. The further the modules 24 are away from the axes of rotation of the head, the more moment of inertia exists when the user moves her head up/down or sideways. A high moment of inertia may shift the mask 10 or pull down on the mask 10.

The locations of the modules 24 on the mask 10 are selected to best fit with the axes of rotation of the head in the up/down and sideways directions. Although the modules 24 are shown under the edges of the eye sockets, in other embodiments, the mask extends further around the face and the modules 24 are along the rear jaw line.

Figure 5:
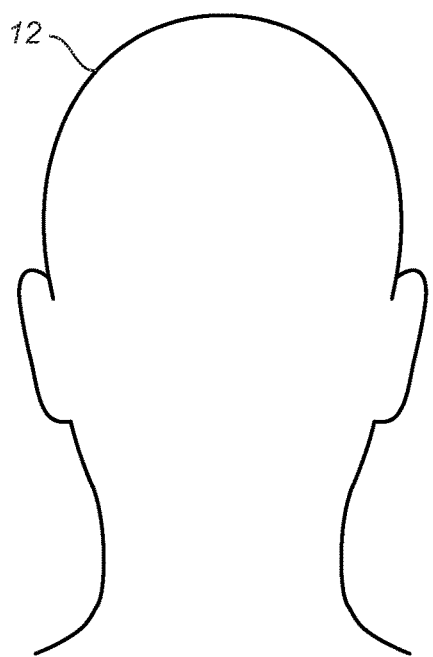
FIGS. 5, 6, 7, and 8 show the relationship between the filtering/electronics module location and the rotational axes of the wearer's head to minimize the moment of inertia of the mask when moving.
Figure 6:
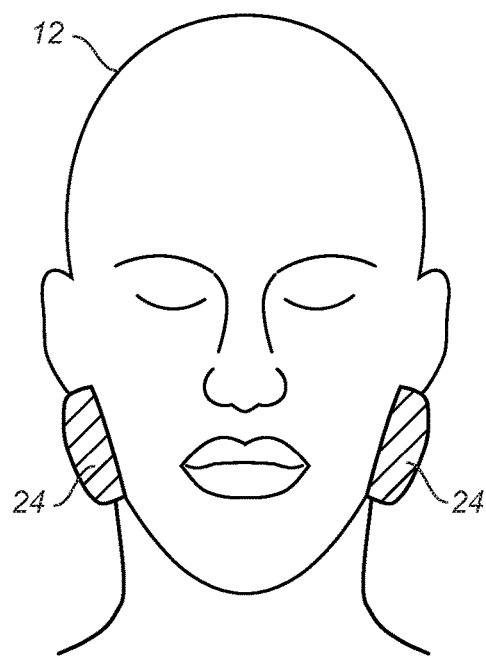
Figure 7:
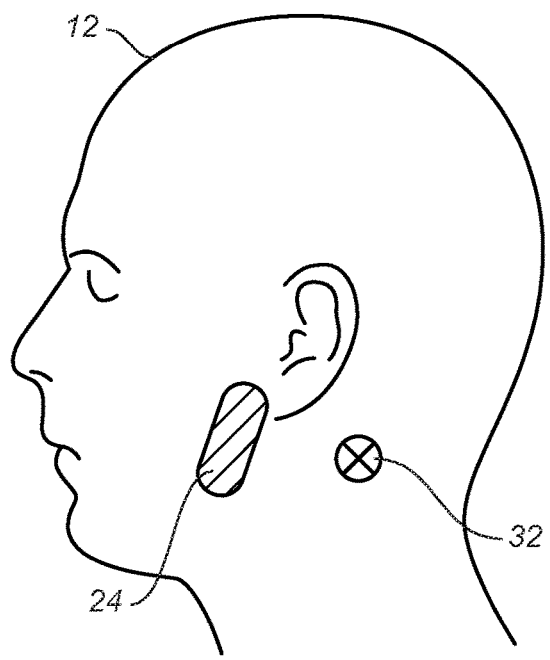
Figure 8:
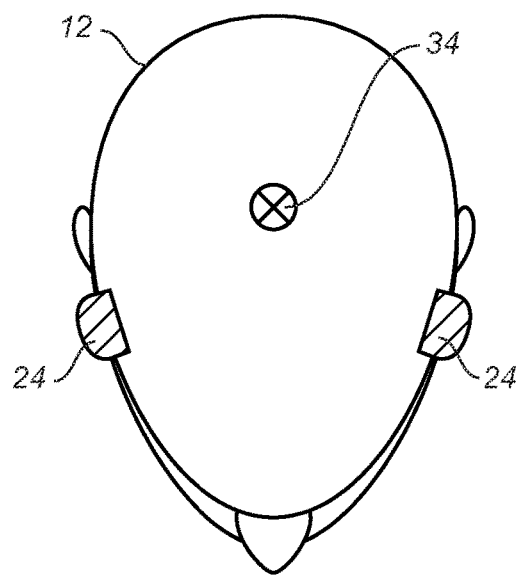

FIGS. 5-8 relate to the locations of the axes of rotation of the head relative to the locations of the modules 24 in one embodiment. FIG. 5 shows the back of the head where the modules 24 are hidden from view. FIG. 6 illustrates the positions of the modules 24 along the rear jaw line. FIG. 7 shows the axis of rotation 32 of the head moving up and down. The modules 24 are as close to the axis of rotation 32 as practical. In one embodiment, the modules 24 are located well behind the nose and between the ear and the edge of the eye socket. In another embodiment, the modules 24 are located approximately below the edge of the eye socket. Generally, the modules 24 are located at the rear of the mask 10. FIG. 8 shows the axis of rotation 34 of the head pivoting around a center line of the head (moving the head sideways). The modules 24 are balanced around the axis of rotation 34 and as close to the axis of rotation 34 as practical. Accordingly, the moment of inertia of the mask 10 is at a minimum. Such arrangement also reduces the downward moment felt by the wearer of the mask.

The modules 24 are optionally removable and fit into a resilient receptacle in the mask 10, where electrical contacts on the receptacle are connectable with electrical contacts in the mask 10 that connect to the battery 26.

Figure 9:
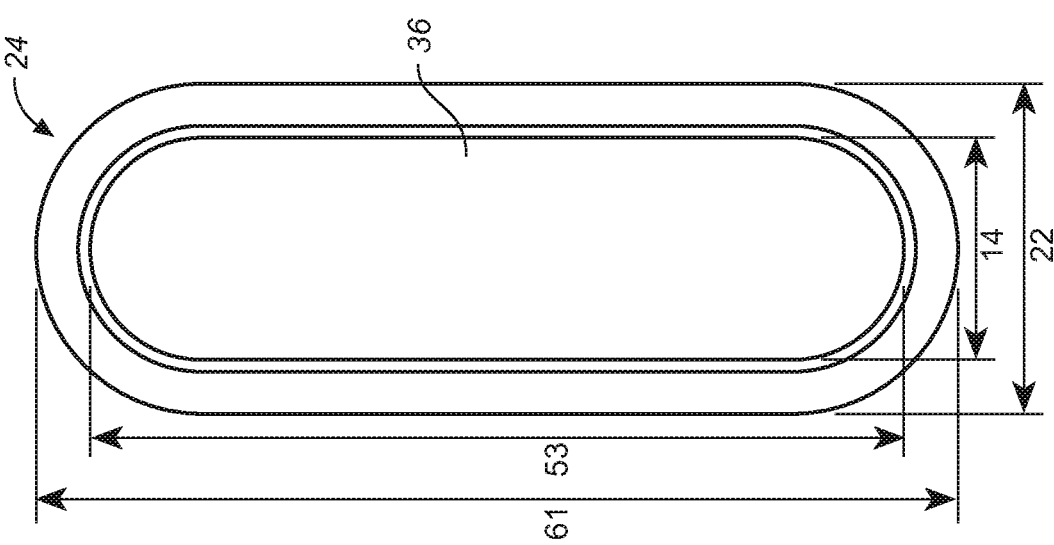
FIG. 9 is a front view of the module showing a thermally conductive grille, having holes or a mesh shape, or a grille having parallel or diagonal heat fins.

FIG. 9 is a front view of a module 24, showing a thermally conductive grille 36 that has relatively wide openings for filtering large particles or aerosol droplets. The grille 36 may have holes, or form a mesh, or have narrow parallel fins. The body of the module 24 is made of light-weight thermally conductive material, such as aluminum or graphite, which is in thermal contact with heat sinks for the UVC LEDs and other electronics and in thermal contact with the metal grille 36. Thus, ambient air flow through the grille 36 removes heat from the module 24.

Dimensions of the module 24 are shown in millimeters.

Figure 10:
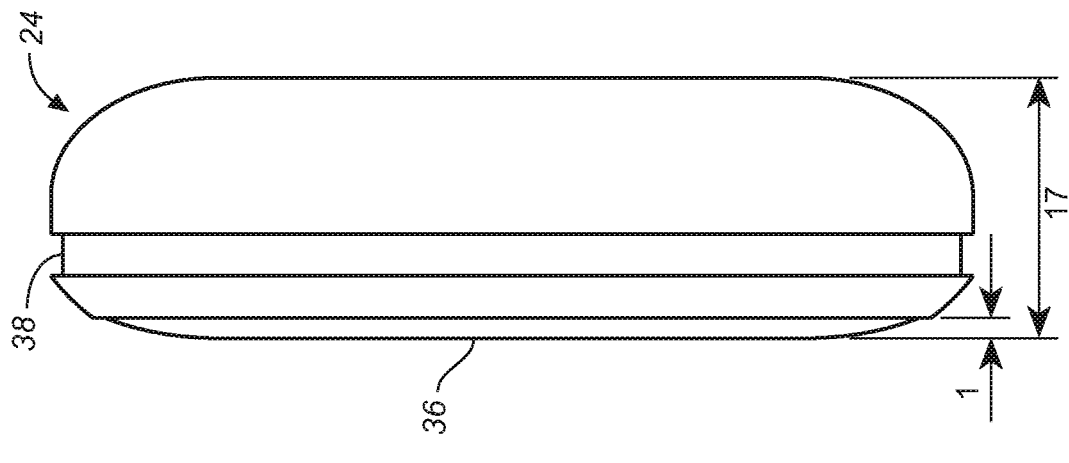
FIG. 10 is a side view of the module.

FIG. 10 is a side view of the module 24. The module 24 has a generally oval shape. Air flow openings are at the top and bottom of the module 24. An indentation 38 receives a resilient seal when installed in the mask 10 for directing air flow through the module 24.

Figure 11:
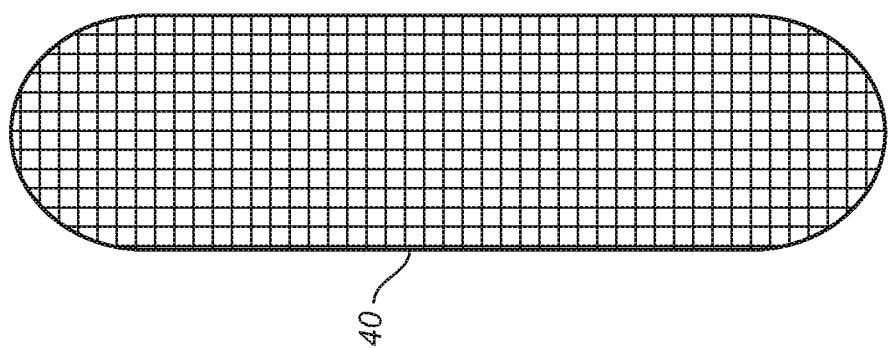
FIG. 11 shows a replaceable air filter that is inserted into the module.

FIG. 11 illustrates a replaceable fine filter 40 that is inserted between the metal grille 36 and the UVC chamber. The filter 40 is fine enough to filter out large particulates or aerosol droplets. However, viruses can be extremely small, such as less than 0.1 micron. A filter with pores less than 0.1 micron may provide too much air resistance to be comfortable to the wearer. The UVC light inactivates such viruses and other organisms so the filter 40 can be formed to have a comfortable air flow resistance.

In one embodiment, the filter 40 has pores having diameters of about 3-10 microns. In another embodiment, the filter 40 has pores having diameters greater than 10 microns.

Figure 12:
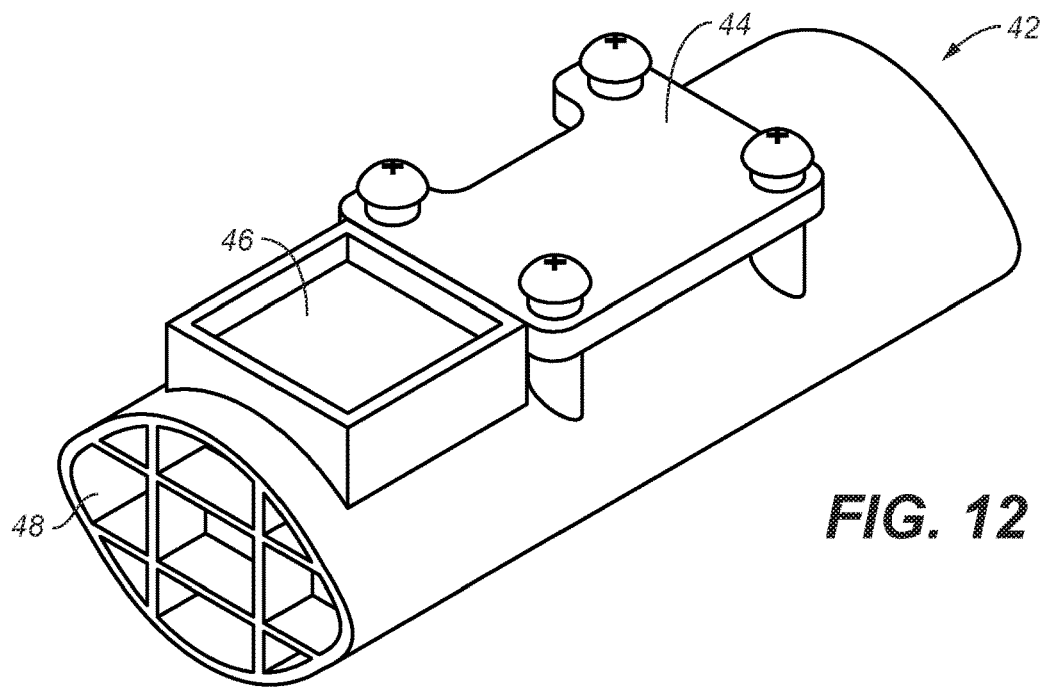
FIG. 12 is a perspective view of the module, showing an air intake opening, where the side facing up is the side facing the metal grille.

FIG. 12 shows an inner chamber 42 of the module 24. The bottom surface of the chamber 42 in FIG. 12 is the rear surface of the module 24 in FIG. 9. The inner oval wall of the chamber 42 (described in detail later) is reflective, and the UVC light is directed within the chamber 42. The UVC LEDs are thermally coupled to a metal heat sink 44. Other circuitry, such as power management and flow rate sensor circuitry are coupled to another metal heat sink 46. The heat sinks 44 and 46 face the metal grille 36 in FIG. 9. The various pieces of the module 24 may be releasably attached directly to the chamber 42, or the resilient receptacle in the mask 10 for the module 24 may mechanically retain the various parts in place.

The opening 48 is preferably where the inhaled air enters the chamber 42 since the opening 48 is closest to the flow rate sensor where the inhaled air has the minimum turbulence. The opening 48 is optionally formed with grilles to help reduce turbulence. By reducing the air turbulence, the flow rate sensor more accurately detects the rate of air flowing through the chamber 42 and the current to the UVC LEDs can be more accurately controlled.

Figure 13:
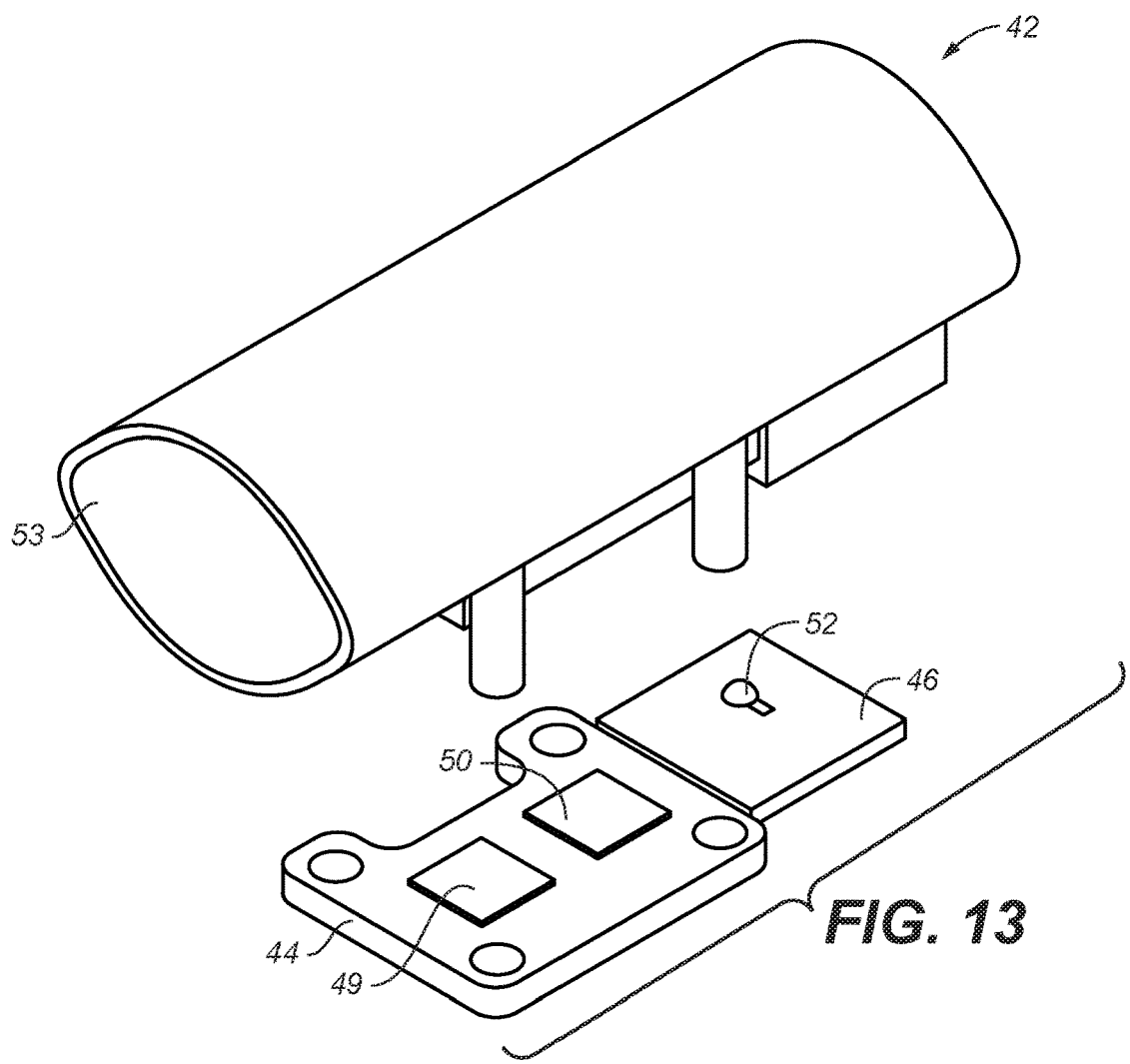
FIG. 13 is a perspective view of the "back" side of the module, showing an air outlet opening.

FIG. 13 shows the other side of the chamber 42 with the heat sinks 44 and 46 removed. Two UVC LED chips 49 and 50 are mounted on the heat sink 44, although only one UVC LED may be needed if it has a high enough output power. Subsequent figures show only one UVC LED per module. The UV LEDs may be linearly arranged along the chamber 42 or side by side. The number of UVC LEDs depends on the required light output power needed to effectively kill at least 99.99% of harmful organisms in the air. A MEMs flow rate sensor 52, along with other circuitry, is mounted on the heat sink 46. The flow rate sensor 52 is substantially thermally isolated from the UVC LEDs, since the flow rate sensor 52 is typically temperature sensitive. The opening 53 will be the exit opening for inhalation.

The exhaled air goes in the opposite direction through the chamber 42. Both directions of air are subjected to the UVC radiation. The mask 10 may be worn by medical staff or patients, so air must be disinfected in both directions.

The heat generated by the various components is thermally coupled to the heat sinks 44/46, which are thermally coupled to the aluminum body of the module 24, which is thermally coupled to the metal grille 36 (FIG. 9). The silicone receptacle for the modules 24 and the straps of the mask are also thermally conductive since they contain thermally conductive particles, such as graphene, copper, aluminum, etc.

Figure 14:
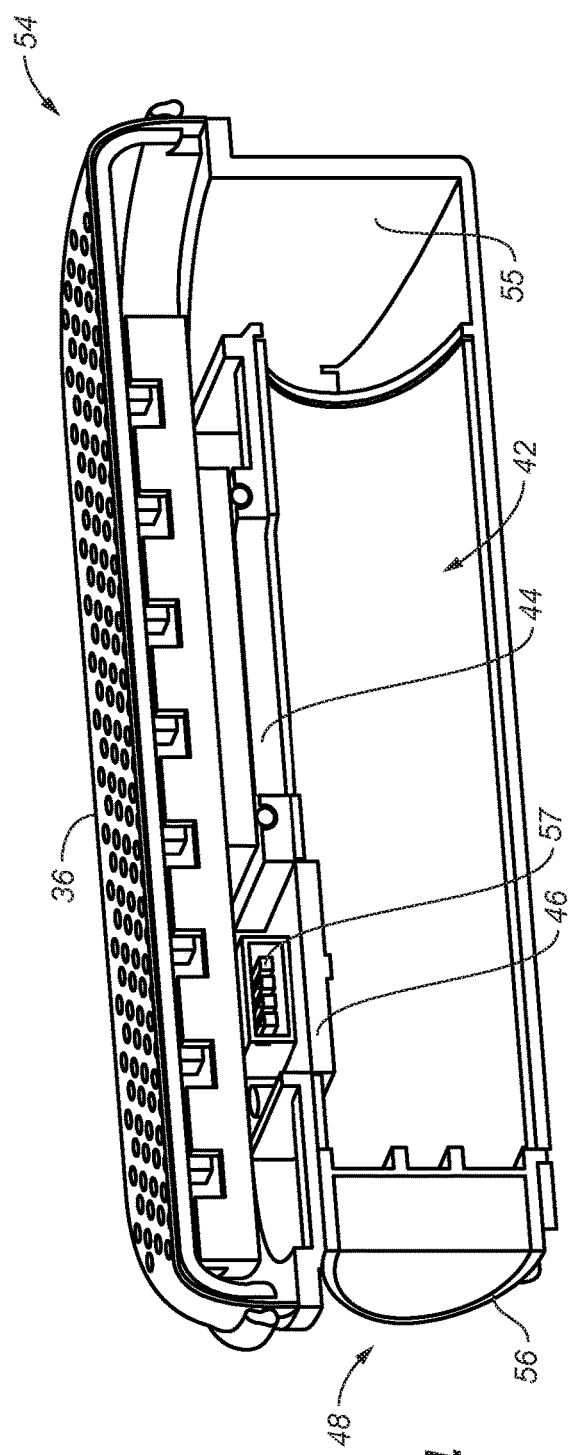
FIG. 14 is a cut-away view of the module showing the reflective inner chamber and a non-reflective L-shaped portion that helps prevents UVC light escaping from the module. A photocatalyst filter at the other end also helps prevent UVC light escaping from the module.

FIG. 14 is a cut-away view of another embodiment of a module 54, showing the reflective chamber 42, the metal grille 36, the UVC LED heat sink 44, the flow rate sensor heat sink 46, an L-shape or U-shape portion 55, and a photocatalyst filter 56. To prevent UVC light from coming in contact with the wearer's skin, a non-reflective L-shape or U-shape portion 55 absorbs the UVC light. The long part of the L-shape includes the inner reflective chamber 42, and the short part of the L-shape (or the part of the U-shape which is anti-parallel to the chamber 42) is the non-reflective portion that absorbs the UVC light. The wearer's exhaled air flows into the chamber 42 through an opening in the module 54 along its side, rather than through its right end. At the other end of the module 54 is an optional porous photocatalyst filter 56 for reacting with the inhaled air. The UVC light causes ionization in the photocatalyst filter 56 that reacts with substances in the air for additional purification. The photocatalyst filter 56 blocks the UVC light from exiting through the opening 48. An electrical connector 57 for at least battery power is also shown.

Figure 15:
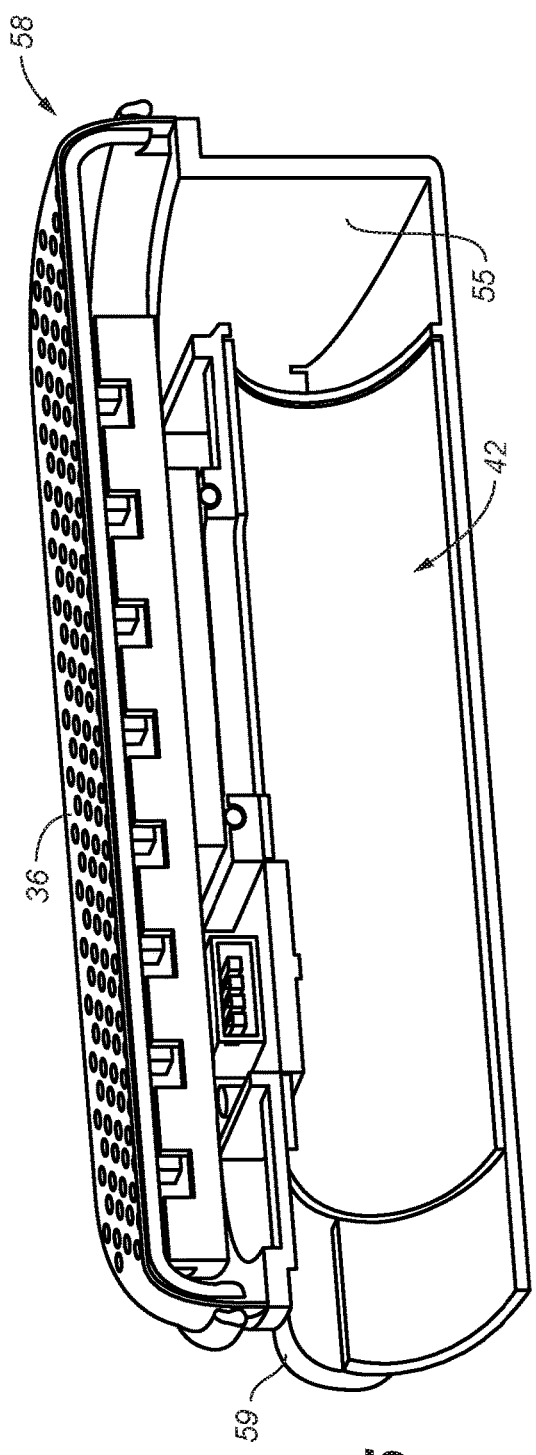
FIG. 15 is a perspective view of another embodiment of the module where a "bottom" part of the thermally conductive shell is extended to better block UVC radiation from impinging on the wearer's skin. The extended portion is sealed within the mask, and the wearer's inhale and exhale air flows across the extended portion.

FIG. 15 is a cut-away view of another embodiment of a module 58 having an extended shell portion 59 that is the air opening into the mask. The extended shell portion 59 helps prevent UVC light directly contacting the wearer's skin.

Figure 16:
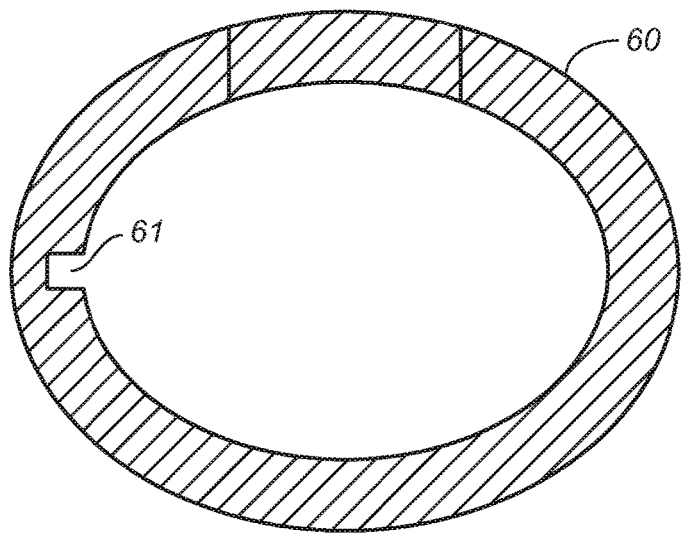
FIG. 16 is a cross-sectional view of the thermally conductive outer shell of the module.
Figure 17:
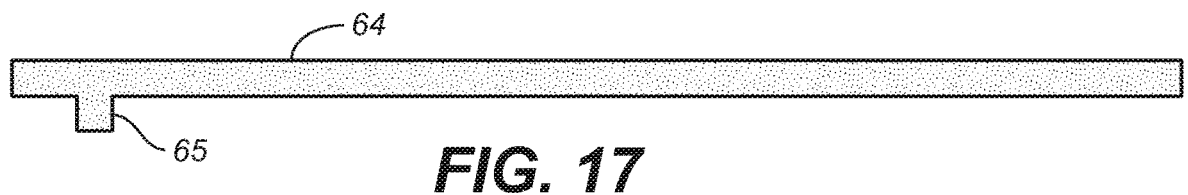
FIG. 17 is a cross-sectional view of a reflective inner lining of the UVC chamber prior to its being inserted into the outer shell.
Figure 18:
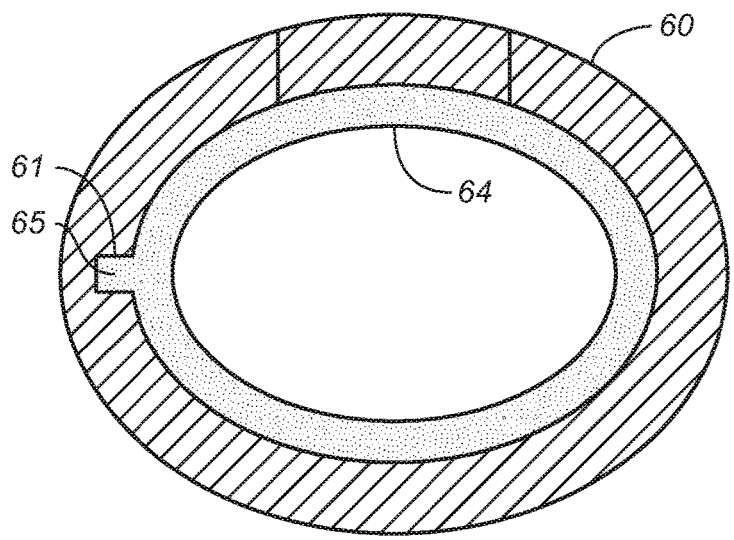
FIG. 18 shows the reflective inner lining bent and inserted into the outer shell, with an alignment tab being used for aligning the two parts.

FIGS. 16-18 apply to either of the embodiments of FIGS. 14 and 15. The reflective chamber 42 (FIG. 15) of the module may be made reflective using a coating or a liner. It is easier to manufacture the reflective layer separately as a liner and then insert the liner into an outer shell of the module. FIG. 16 is a cross-section of the thermally conductive outer shell 60 of the module. An alignment notch 61 is formed in the inner wall.

FIG. 17 is a cross-section of a flat reflective layer 64, such as polytetrafluoroethylene (PTFE), barium sulfate, a metal, or other material that is manufactured as a sheet. The surface may be diffusively reflective or specular. By making the surface diffusively reflective, there is less reflection loss in cold weather when water vapor may condense on the inner wall. The reflective layer 64 contains an alignment tab 65. Suitable openings are formed in the reflective layer 64 and the outer shell 60 for the flow rate sensor and UVC LEDs.

In FIG. 18, the reflective layer 64 is bent and inserted into the outer shell 60. The alignment tab 65 is inserted into the alignment notch 61. The inner walls are as smooth as practical to minimize turbulence.

FIG. 19 is a cutaway view of the inside of the mask 10, where the module 58 (shown in more detail in FIG. 15) is shown inserted into an air-tight resilient receptacle 66. The translucent front of the mask 10 is surrounded by a soft silicone edge 68 that forms an air-tight seal around the wearer's face. All air 69 flowing into and out of the mask 10 flows through the modules 58 via the extended shell portion 59, the inner reflective chamber 42 (FIG. 15), and the thermally conductive grill 36. The extended shell portion 59 blocks UVC radiation from directly contacting the wearer's skin.

Figure 21:
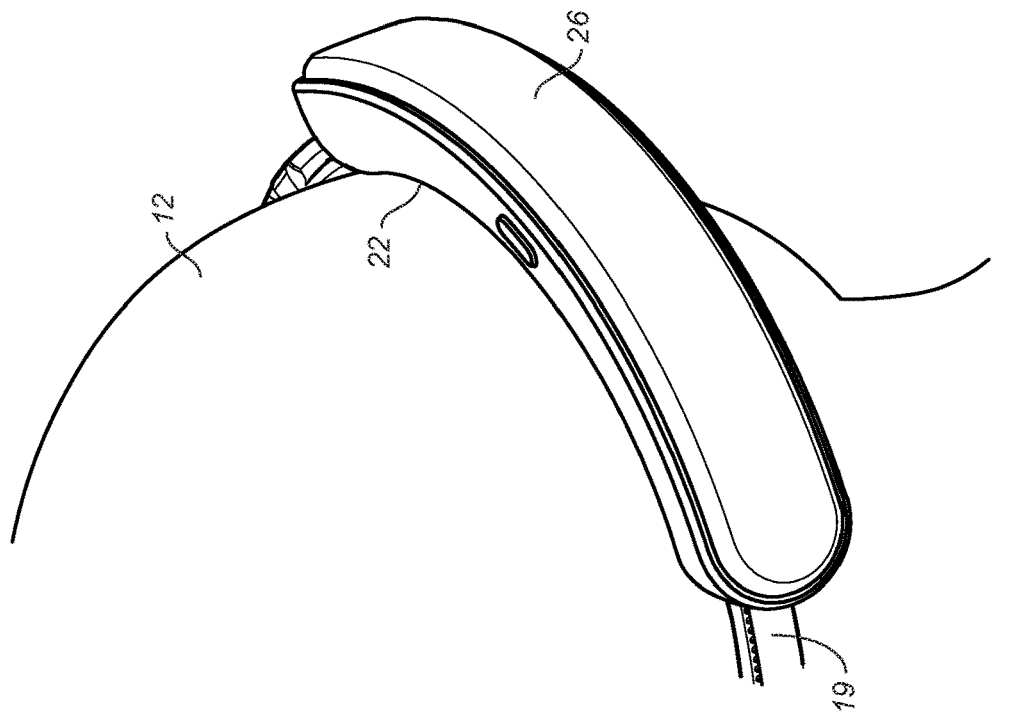
FIG. 21 shows the battery pack connected to the silicone pad and strap.
Figure 20:
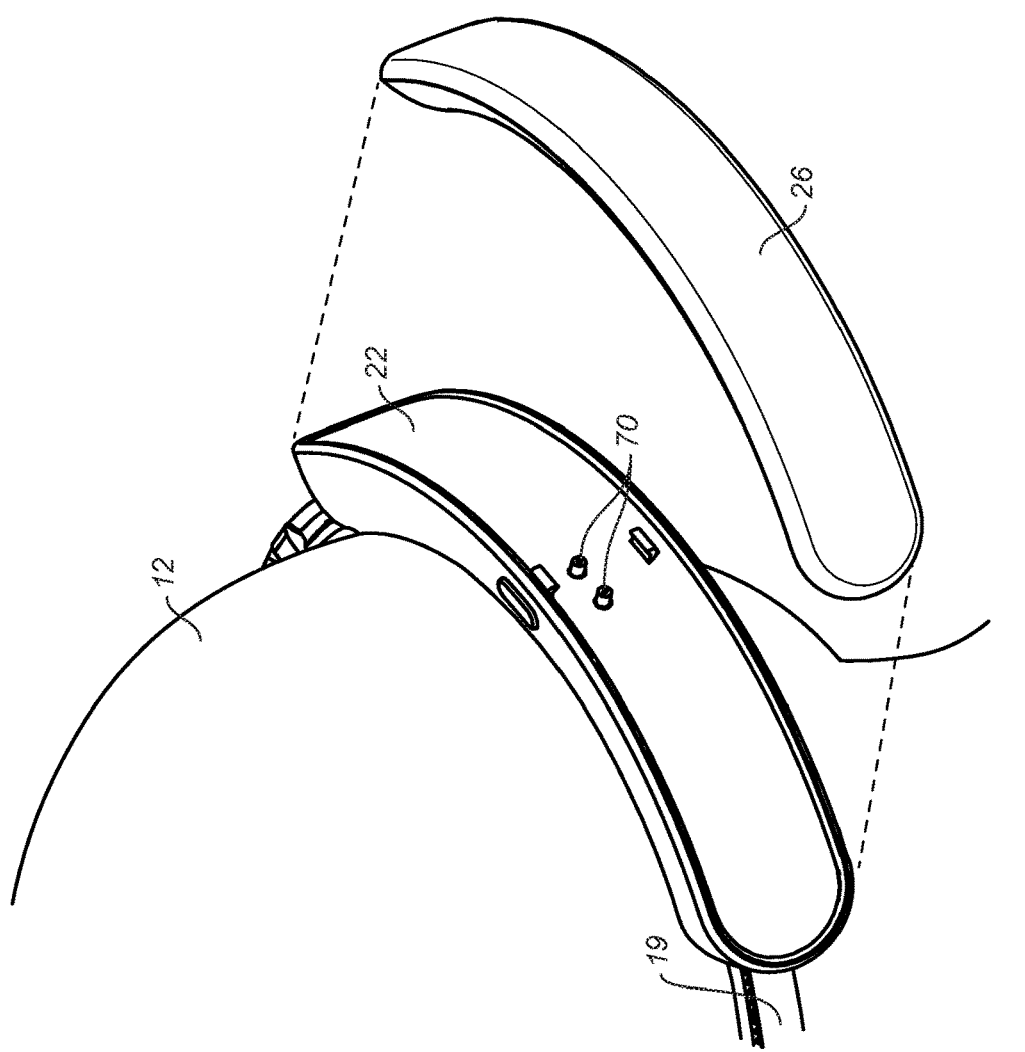
FIG. 20 shows the battery pack disconnected from a soft silicone pad that receives the back of the strap.

FIG. 20 illustrates the replaceable battery 26 removed from the mask, and FIG. 21 shows the battery 26 attached to the mask. The battery 26 attaches to a soft silicone pad 22. Electrodes of the battery 26 contact electrodes 70 on the pad 22. The electrodes 70 lead to an electrical connector in the mask receptacle, which connects to a conventional electrical connector provided along the side of the module, which electrically connects to electrodes (FIG. 22) of the modules electronics. The battery power is conducted by wires along the mask straps 19 (FIG. 1). The wires may be laminated in the straps 19 in a serpentine path to allow the straps 19 to stretch and bend or another type of flexible circuit may be formed in the straps 19. The battery 26 may be recharged using a USB cable or can be charged wirelessly.

FIGS. 1-4, 20, and 21 depict the battery 26 connected to the disinfection chamber(s) through the upper head strap. However, it should be understood that the battery may also be connected to the disinfection chamber(s) through the lower head strap.

A vibrating (haptic) element may be installed in the battery 26 to signal to the wearer that the battery 26 has, for example, only 10% reserve power or 15 minutes of life left. An audible warning may instead be used but may be difficult to discern in a noisy environment.

Figure 22:
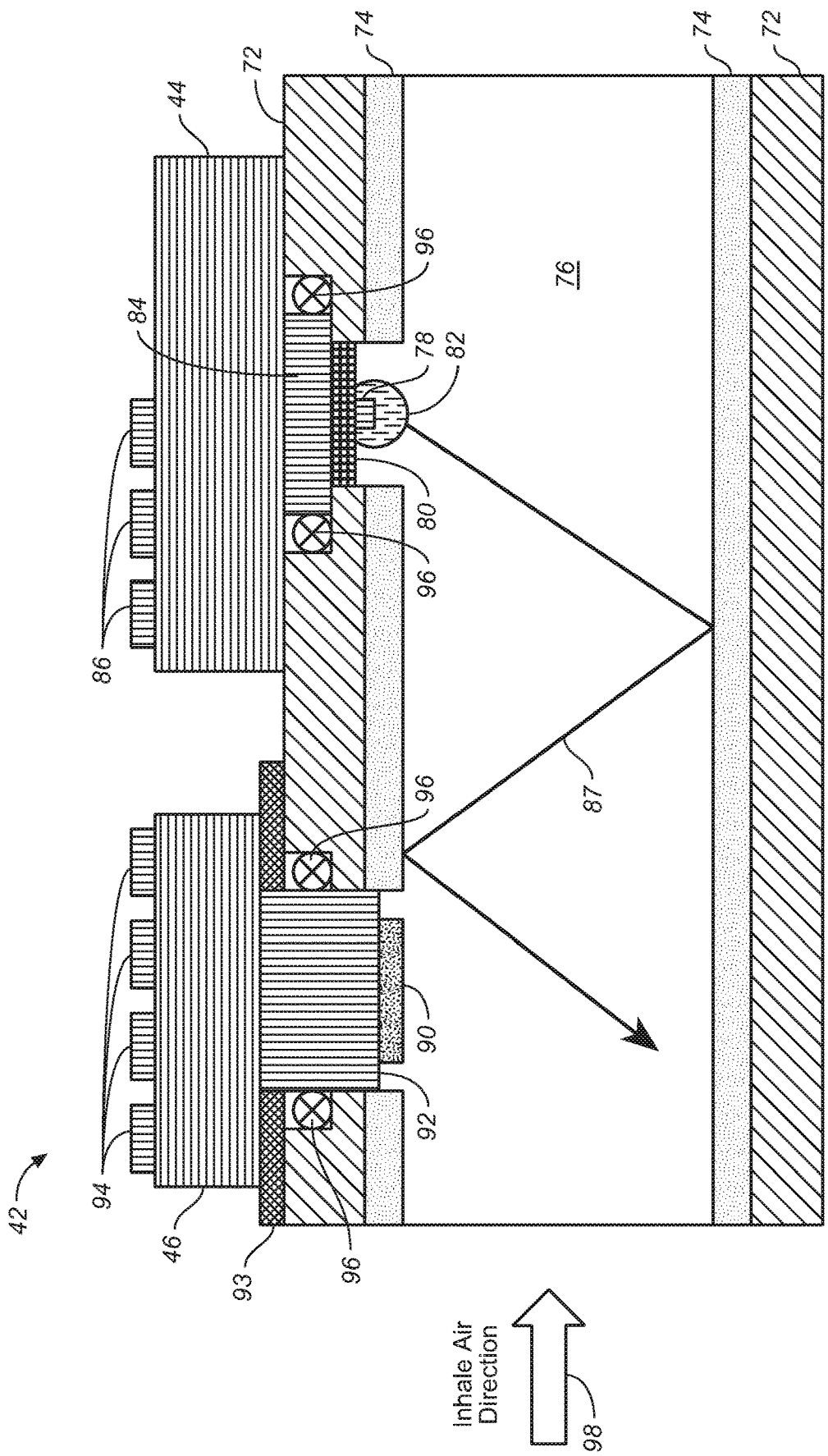
FIG. 22 is a cross-sectional view of the module's air flow chamber, UVC LEDs, heat sink, flow rate sensor, and control electronics.

FIG. 22 is a cross-sectional view of the chamber 42 of the module 24 or 58. The outer body 72 is a thermally conductive material, such as copper, aluminum, other metals, graphite, or thermally conductive ceramic materials, for conducting heat. A reflective coating 74 or reflective liner (previously described) forms the inner wall of the air flow passage 76. A UVC LED 78 is on a mount 80 and encased in a dome lens 82. The UVC LED mount 80 is, in turn, connected to a buried circuit 84 which provides more robust connections and good heat spreading. A heat sink 44 is thermally coupled to the buried circuit 84. Electrodes 86 are provided for driving and sensing the performance status of the UVC LED 78. Wiring to the electrodes 86 may be via a printed circuit board or wires.

The UVC LED 78 is recessed in the inner wall of the chamber 42 so as not to add turbulence. The lens 82 is substantially flush with the inner wall of the chamber 42. A light ray 87 is shown reflecting off the reflective coating 74.

A MEMS flow rate sensor 90 senses the flow of air in the chamber 42. There are various suitable designs of flow rate sensors 90. A suitable flow rate sensor 90 is available from Digikey Electronics, Mouser Electronics, Arrow Electronics, or other suppliers. Flow rate sensors typically operate by detecting how much current is needed to keep a heater at the same temperature as the air flow cools the heater. The heater may be a resistive element whose resistance is proportional to temperature. Other types of flow rate sensors detect the temperature difference between two temperature sensors, where the difference increases with more air flow.

The flow rate sensor 90 is connected to a mount 92 that may contain various circuits including the flow rate sensor controller, power management circuits (e.g., current limiters, regulators, etc.), and the UVC LED 78 controller. The mount 92 is coupled to a heat sink 46. An optional thermal insulation layer 93 limits the heating of the flow rate sensor 90 by blocking the thermal conduction from the nearby LEDs. Electrodes 94 lead to the UVC LED electrodes 86, battery (via standard connectors), and possibly other circuits.

Air seals 96, such as O-rings, are shown that seal off the chamber 42.

The arrow 98 illustrates the preferred direction of inhaled air since there is a minimum of turbulence at the entrance near the flow sensor 90. Since, as will be described later, the detected air flow is generally proportional to the current supplied to the UVC LEDs 78, the air flow detection is more accurate when there is less air turbulence, therefore the disinfection rate is better controlled to match the real flow rate of the air. Locating the flow rate sensor 90 close to the inlet where air is less perturbed results in significant reduction of reported flow rate fluctuations, and this should result in more accurate control of current to the UVC LED 78.

As previously described, the heat generated by the components is spread over the thermally conductive body of the module 24, coupled to the thermally conductive grille 36 (FIG. 9), and coupled to the thermally conductive mask receptacle 58 (FIG. 19) and mask straps 19/20 (FIG. 1). The thermally conductive materials may include aluminum or copper alloys, graphite, carbon, ceramics, plastic matrix infused with carbon or metal particles, etc.

Figure 23:
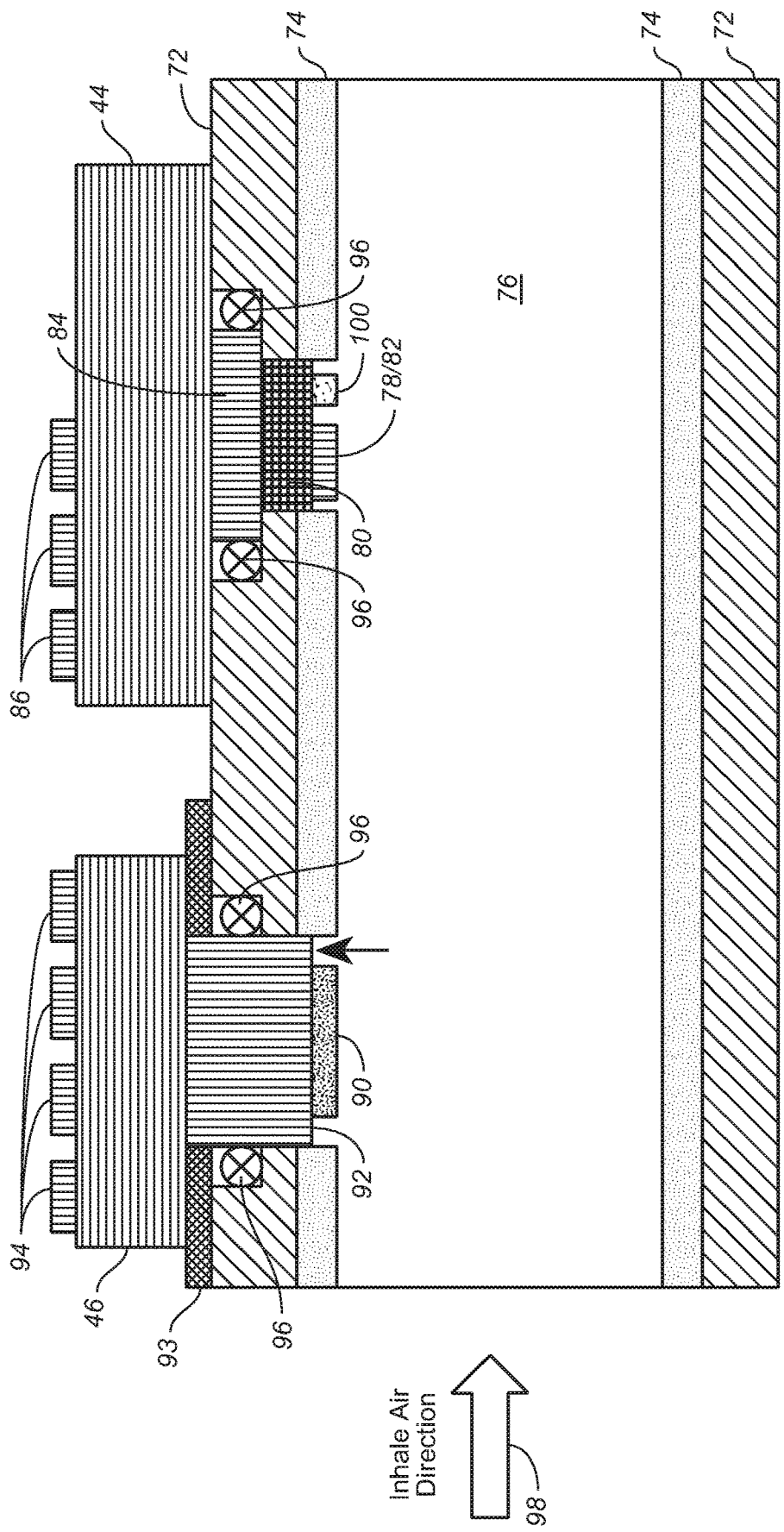
FIG. 23 is similar to FIG. 22 but additionally shows photodetectors for ensuring proper operation of the UVC LEDs.

FIG. 23 is similar to FIG. 22 except that a photodetector 100 is added that provides feedback regarding the output of the UVC LED 78. Over time, the UVC LED 78 becomes less efficient, or the reflective coating or the reflective inner chamber becomes tarnished by oxygen or moisture. The photodetector 100 provides feedback signals to the UVC LED controller to maintain the same light power over the lifetime of the mask. The photodetector 100 senses the intensity of the direct or waveguided light from the neighboring LED and reflected light from the reflective wall to suitably adjust the power of the LED to compensate any performance degradation. In the event of failure of the UVC LED 78, the feedback may produce an audible or haptic signal.

Figure 24:
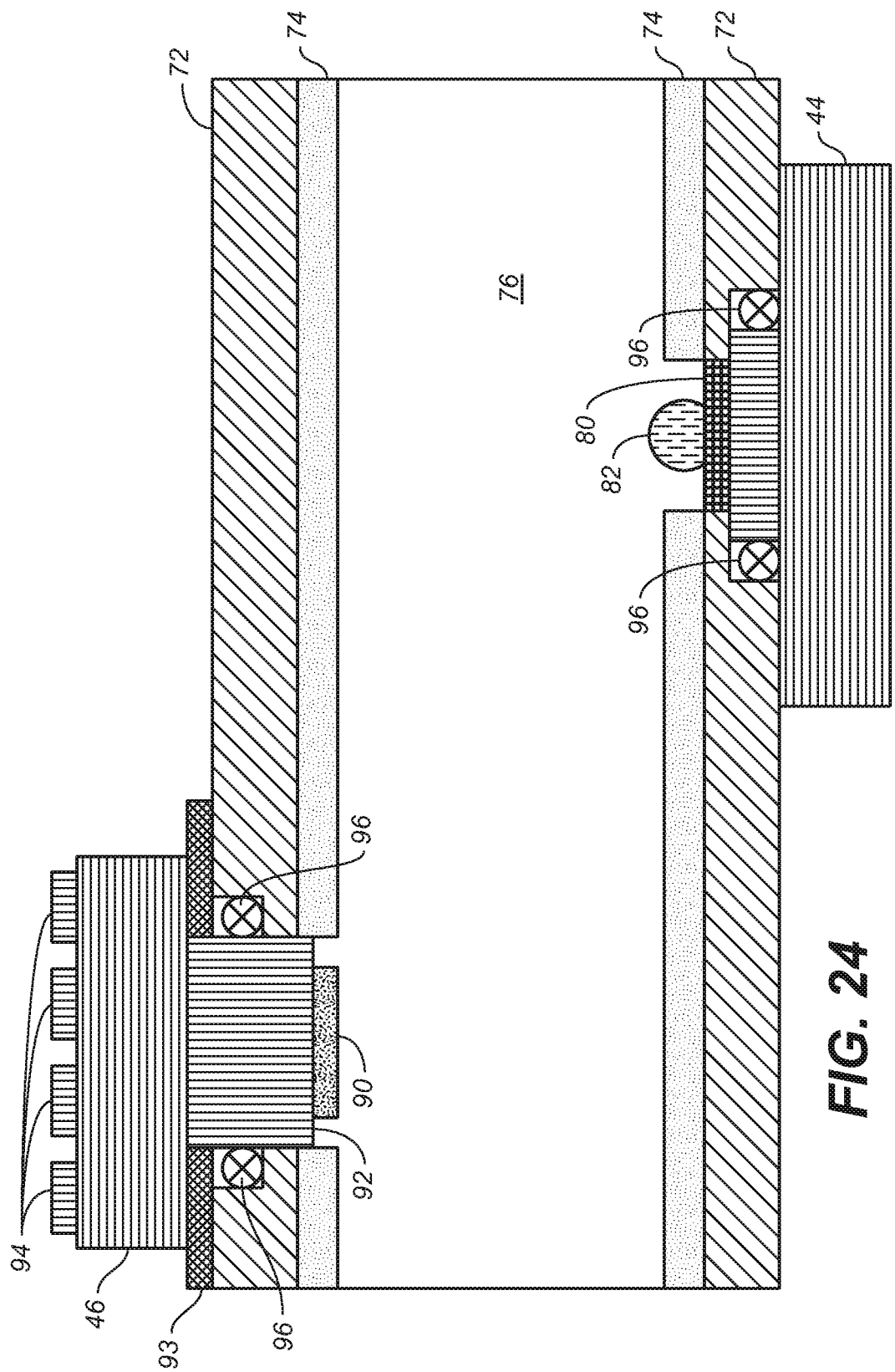
FIG. 24 shows the UVC LEDs and flow rate sensor on opposite sides of the air passage to reduce turbulence near the flow rate sensor.

If accurate bi-directional flow rate sensing is desired, the embodiment shown in FIG. 24 may be used. FIG. 24 illustrates how the UVC LED portion may be installed on the opposite side of the chamber as the flow rate sensor 90 to further reduce turbulence at the flow rate sensor 90 due to any turbulence created by the opening in the chamber for the UVC LED lens 82.

Figure 25:
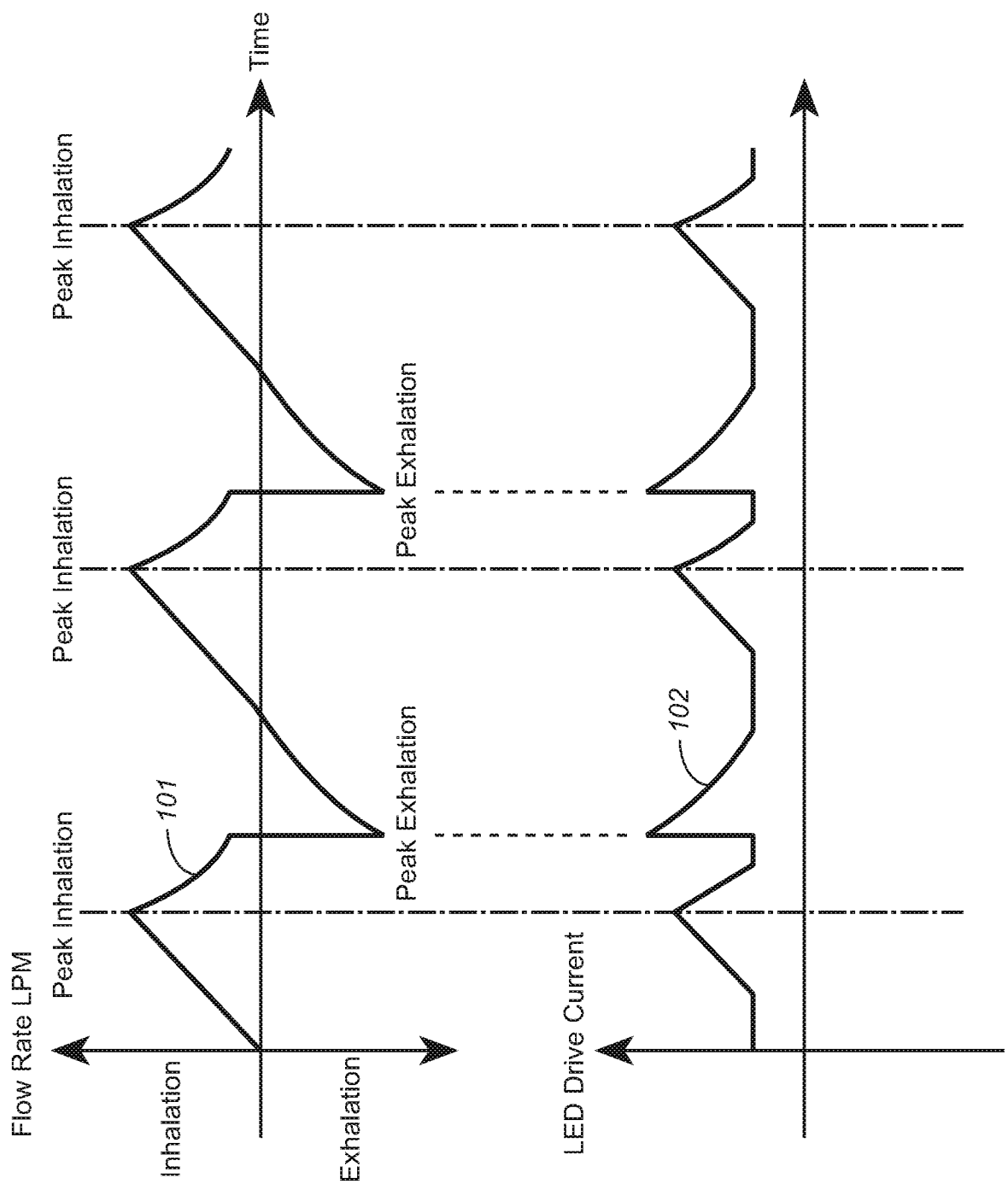
FIG. 25 illustrates the relationship between the detected air flow by the flow rate sensor and the level of current provided to the UVC LEDs by a control circuit.

FIG. 25 illustrates the relationship between the detected air flow rate 101 and drive current 102 to the UVC LEDs. A controller circuit optionally housed in the module 24, and connected through the mount 92 in FIG. 22, receives signals from the flow rate sensor 90 and generates a continuous or pulse-width modulated current for the UVC LEDs to cause the current to the UVC LEDs to be generally proportional to the air flow. This greatly extends battery life, reduces heat, and ensures that there is sufficient UVC light power to inactivate a high percentage of microorganisms in the air flow. As the stagnant boundary layer may lead to a slight under-reporting of the flow rate, a deliberate off-set of the air speed maybe performed. Such off-set can be +5%, or can be +30% if higher margin of safety is preferred.

Below a low threshold of air flow, given in liters per minute (LPM), the UVC LEDs are supplied a fixed low average or instantaneous current to avoid the UVC LEDs repeatedly turning on and off (flickering), such as when the wearer is calm and talking. This threshold may be about 0.8 LPM. As the inhale flow rate increases, the supplied current to the UVC LEDs is increased. The current then drops to a minimum non-zero value as the inhalation rate decreases. Similarly in the exhalation portion of the breathing cycle, as the exhale flow rate increases, the supplied current to the UVC LEDs is increased. The current then again drops to a minimum non-zero value as the exhalation rate decreases and the air flow direction reverses. Periodically, the flow rate/current relationship may be verified with biological tests to ensure that adequate inactivation is achieved for typical daily use and temporary emergency situations.

Figure 26:
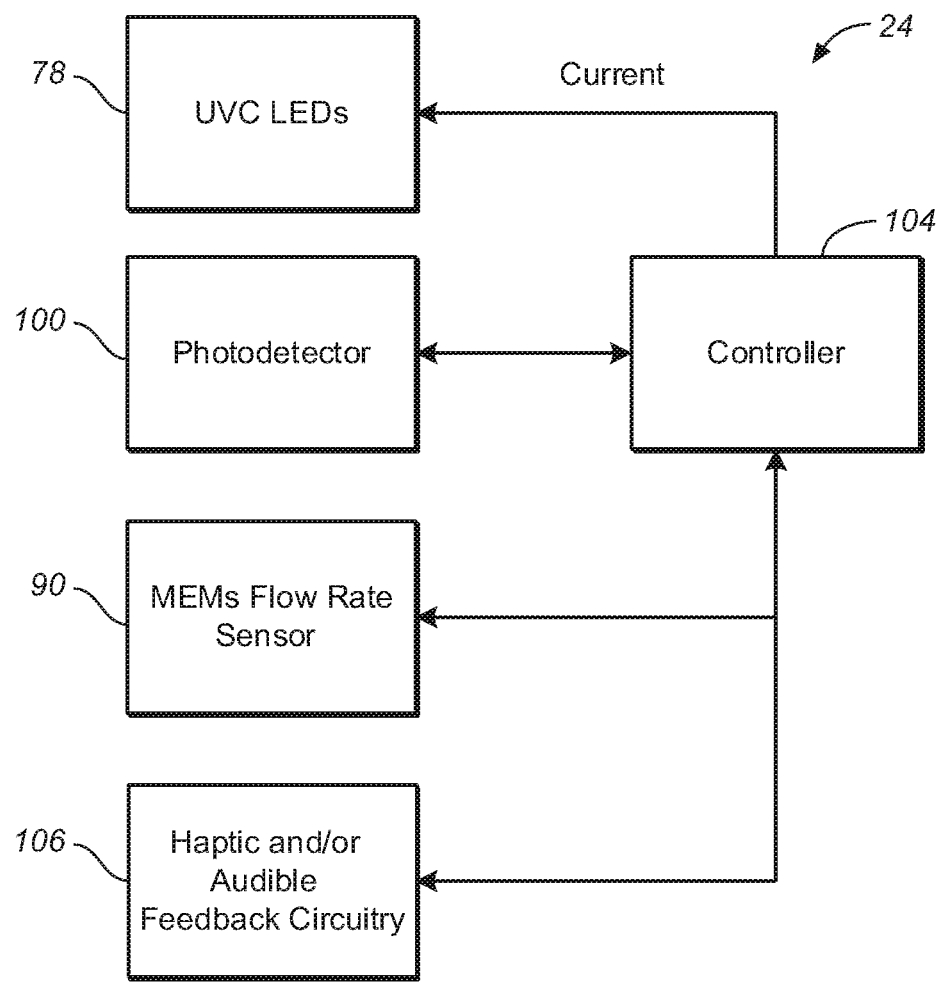
FIG. 26 is a schematic diagram of the electronics in the module.

FIG. 26 illustrates the basic circuitry within the module 24. The UVC LED controller 104 receives feedback signals from the photodetector 100 and flow rate sensor 90 and controls the UVC LEDs 78 accordingly, as described above. The UVC LED controller 104 can also monitor both the current and voltage of the LEDs and flow rate sensors to provide warning in case of device malfunction. Block 106 represents haptic (e.g., vibrations) and/or audible feedback circuitry that identifies to the wearer a low battery, UVC LED problem, time to replace filter, or other maintenance issue.

Any of the features described above may be combined into a mask. The requirements of the mask may change depending of the level of protection desired.

Having described the invention in detail, those skilled in the art will appreciate that, given the present disclosure, modifications may be made to the invention without departing from the spirit of the inventive concept described herein. Therefore, it is not intended that the scope of the invention be limited to the specific embodiments illustrated and described.

What is claimed is:

1. A protective mask comprising:
   a transparent or translucent covering for at least a wearer's nose and mouth;
   one or more straps connected to the covering being configured to extend at least partially around the wearer's head;
   a first module, the first module being located proximate an edge of the covering and configured to be located below at least a portion of an eye socket of the wearer or between the eye socket and an ear of the wearer, the first module comprising:
   at least one UVC light emitting diode (LED);
   a reflective chamber receiving UVC light from the LED;
   a flow rate sensor in the chamber for detecting a flow rate of inhaled and exhaled a flowing through the chamber; and
   a controller configured for receiving first signals from the flow rate sensor and controlling a current to the LED, wherein, when there is an increased inhale and exhale by the wearer, the controller is configured to supply an increased current to the LED,
   wherein the controller is configured to supply a non-zero minimum current to the LED when the inhale or exhale flow rate is detected to be below a threshold flow rate, including a zero flow rate.

2. The mask of claim 1 wherein the current to the LED is a continuous or average current.

3. The mask of claim 1 further comprising a filter located at one end of the reflective chamber.

4. The mask of claim 1 wherein the flow rate sensor is located upstream of an LED for inhaled air.

5. The mask of claim 1 wherein the LED and the flow rate sensor are along a same side of the reflective chamber.

6. The mask of claim 1 wherein the LED and the flow rate sensor are along opposite sides of the reflective chamber.

7. The mask of claim 1 wherein the first module has a thermally conductive body that conducts heat away from the LED, wherein the body is substantially thermally insulated from the flow rate sensor.

8. The mask of claim 1 further comprising a second module, identical to the first module, wherein the first module is configured to be located below at least a portion of a right eye socket of the wearer, and the second module is configured to be located below at least a portion of a left eye socket of the wearer.

9. The mask of claim 1 further comprising a second module, identical to the first module, wherein the first module is configured to be located approximately below an edge of the right eye socket of the wearer, and the second module is configured to be located approximately below an edge of the left eye socket of the wearer.

10. The mask of claim 1 further comprising a thermally conductive grille through which inhaled air and exhaled air flows, the grille being thermally coupled to the LED for removing heat from the LED.

11. The mask of claim 1 wherein the first module includes an L-shaped or U-shaped air passage, wherein the reflective chamber forms a long part of the L-shape or U-shape, and a non-reflective portion of each module forms a short part of the L-shape or U-shape.

12. The mask of claim 1 further comprising a lens for the LED, where the lens is substantially flush with the reflective chamber to reduce turbulence.

13. The mask of claim 1 further comprising a photodetector in the first module, wherein the photodetector generates second signals, and wherein the second signals from the photodetector are received by the controller to determine the operation of the LED.

14. The mask of claim 1 wherein there are at least two UVC LEDs in the first module.

15. The mask of claim 1 further comprising:
   a battery providing power to the first module; and
   feedback circuitry that provides an audible or haptic feedback signal to the wearer in an event of a malfunction or low battery power.

* * * * *